(12) United States Patent
Lobel

(10) Patent No.: US 10,945,982 B1
(45) Date of Patent: *Mar. 16, 2021

(54) NASAL HYGIENE METHOD AND COMPOSITION

(71) Applicant: Paul A. Lobel, Ashton, MD (US)

(72) Inventor: Paul A. Lobel, Ashton, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/403,262

(22) Filed: May 3, 2019

Related U.S. Application Data

(60) Provisional application No. 62/666,561, filed on May 3, 2018.

(51) Int. Cl.
*A61K 31/201* (2006.01)
*A61K 31/202* (2006.01)
*A61K 33/14* (2006.01)
*A61K 33/20* (2006.01)

(52) U.S. Cl.
CPC .......... *A61K 31/201* (2013.01); *A61K 31/202* (2013.01); *A61K 33/14* (2013.01); *A61K 33/20* (2013.01)

(58) Field of Classification Search
CPC .......... A61K 33/40; A61K 45/06; A61K 9/08
USPC ....................................... 514/20.5
See application file for complete search history.

(56) References Cited

U.S. PATENT DOCUMENTS

| | | |
|---|---|---|
| 5,334,383 A | 8/1994 | Morrow |
| 5,622,848 A | 4/1997 | Morrow |
| 5,736,165 A | 4/1998 | Ripley et al. |
| 5,738,840 A | 4/1998 | Richter |
| 6,387,344 B1 | 5/2002 | Tenney et al. |
| 6,410,588 B1 * | 6/2002 | Feldmann ............ A61K 31/352 514/454 |
| 7,029,705 B2 | 4/2006 | Fuhr |
| 7,491,383 B2 * | 2/2009 | Woodward ........... A61K 47/542 424/78.08 |
| 2011/0115166 A1 * | 5/2011 | Grobler .................. C09K 17/18 277/316 |
| 2017/0105934 A1 * | 4/2017 | Mizutare ................ A61K 47/02 |

FOREIGN PATENT DOCUMENTS

| | | | |
|---|---|---|---|
| WO | WO2016162894 | * 10/2016 | ............. A61K 9/00 |
| WO | WO2017210454 | * 12/2017 | ............. A61K 33/40 |

OTHER PUBLICATIONS

Chemical Abstracts 136:74583; abstracting CN 1296819 (2001).

* cited by examiner

*Primary Examiner* — Walter E Webb
(74) *Attorney, Agent, or Firm* — Kutak Rock LLP

(57) ABSTRACT

A composition for and method of practicing nasal hygiene to wash and moisturize the nasal passage. Where the nasal wash comprises a liquid homogenized compound of water, chlorine dioxide (or source thereof), olfactory stimulants, unsaturated fatty acids, inorganic salt, fixing agents. Where the unsaturated fatty acid component comprises from 0.1% to 3% by weight of the compound.

2 Claims, No Drawings

US 10,945,982 B1

NASAL HYGIENE METHOD AND COMPOSITION

This application claims priority pursuant to 35 U.S.C. 119(e) to U.S. Provisional Patent Application Ser. No. 62/666,561 filed May 3, 2018, the entire disclosure of which is incorporated herein by reference.

FIELD OF THE INVENTION

This invention relates to a method of practicing hygiene of the human nose and a composition for use in practice of the method of the invention.

BACKGROUND OF THE INVENTION

The nose is a vital organ, but is often ignored. The nose is responsible for filtering, warming, and humidifying the air one breaths. Increased air pollution overwhelms the natural function of the nose. Air pollution, including ozone, nitric oxide, and nitrogen dioxide can cause lung injury if they are not filtered by the nose. The condition of dry nose reduces the natural filtering and humidifying function of the nose.

In the United States, nasal hygiene is rarely practiced as a daily or even frequent periodic routine. Daily nasal hygiene is a known method to help clean the nasal passages. However, none of the known solutions for nasal hygiene provide moisturizing compounds and antioxidant compounds.

Plain water, the universal cleanser, turns out to be a poor choice for nasal hygiene. As pointed out by Douglas Hoffman MD, while salt solutions containing higher concentrations than body tissues (so-called hypertonic solutions) draw water out of the tissues, plain water has the opposite effect, entering the tissues and adding to the swelling pressure. Saline solutions, on the other hand, need careful regulation to avoid levels of salt that irritate healthy and particularly inflamed tissues.

In ear-nose-throat clinics, patients have had noses rinsed with dilute potassium permanganate solutions for disinfecting purposes. This procedure required using large volumes of rinse solution, and users underwent the inconvenience of catching and disposing of the spent solution after use.

SUMMARY OF THE INVENTION

In accordance with this invention, there is provided an improved method of practicing nasal hygiene comprising the steps of applying to a person's nostril a non-irritating hygienic composition consisting essentially of a product of compounding under homogenizing conditions water, 0.01% to 5% by weight, as chlorine dioxide, or a source of chlorine dioxide; 0.01% to 3% by weight (combined) of at least three olfactory stimulants; 0.01% to 1% by weight of at least one unsaturated fatty acid; 0 to 5% by weight of at least one fixative compound less volatile than the olfactory stimulant; and 0.1 to 2.5% by weight of at least one inorganic salt selected from the group consisting of alkali metal chloride, alkali metal bicarbonate, and alkali metal chlorate; holding the composition within the nostril for a hygienic holding period, and discharging the composition from the treated nostril.

There is also provided, in accordance with this invention, a novel non-irritating hygienic composition consisting essentially of a product of compounding under homogenizing conditions water, 0.01% to 5% by weight, as chlorine dioxide, or a source of chlorine dioxide; 0.01% to 3% by weight of at least one olfactory stimulant, 0.01% to 1% by weight of at least one unsaturated fatty acid; 0 to 5% by weight of at least one fixative compound less volatile than the olfactory stimulant; and 0.1 to 2.5% by weight of at least one inorganic salt selected from the group consisting of alkali metal chloride, alkali metal bicarbonate, and alkali metal chlorate.

It has been found that the ingredients of the composition interact cooperatively to provide an enhanced beneficial effect to the user beyond the individual effect of each individual ingredient. The inclusion of an unsaturated fatty acid in particular enhances the effect of the other ingredients. The nature of the interaction is not fully understood. It is believed that the combination of chlorine dioxide with the unsaturated fatty acid functions in the composition of the invention by activating and enhancing the effectiveness of one or more other components of the composition.

The addition of at least one unsaturated fatty acid to the composition increases the moisturizing effect of the composition on the nasal passages and reduces oxidizing air pollution. The addition of at least one unsaturated fatty acid also enhances the ability of the nasal passages to filter particulate matter from polluted air. Preferably, the unsaturated fatty acid is a monounsaturated fatty acid, such as omega-7 fatty acids and omega-9 fatty acids, or a polyunsaturated fatty acid, such as omega-3 fatty acids. The compound may also contain combinations of monounsaturated fatty acid and polyunsaturated fatty acid.

Preferably, the composition comprises plant based sources of unsaturated fatty acid.

The term "consisting essentially of" is used in its art-recognized meaning to indicate that the composition is open only to such additional ingredients as do not adversely affect its beneficial properties. In particular, such ingredients, and concentrations of ingredients, as render the composition irritating to the mucous membrane inside the nose, are excluded. As an example of an additional ingredient that does not adversely affect the beneficial properties and can enhance the benefit of the composition, a fixative compound less volatile than the olfactory stimulant is given.

The term "product compounded under homogenizing conditions" defines a product that has been subjected to heat treatment and mechanical action sufficient to minimize a tendency to separate into two liquid phases. Heat treatment at moderately elevated temperatures in the range of 30 to 55.degree. C. for a period of 1 to 2000 seconds is generally sufficient. Equipment for applying mechanical action is well known in the art and commercially available.

By practicing nasal hygiene by the use of the method and composition of the invention, nasal irritation is reduced. Daily flushing or washing out the nose according to the invention has been found through testing to moistures the nasal passages. It is believed the increased moisturization of the nasal passage allows the nasal passage to better filter air.

DESCRIPTION OF THE PREFERRED EMBODIMENTS

In the preferred embodiments of the invention include a source of chlorine dioxide. The inclusion of chlorine dioxide in nasal spray is described in U.S. Pat. No. 7,029,705 and is hereby incorporated by reference. The preferred embodiment includes sufficient chlorine dioxide source to provide 0.01 to 5% by weight chlorine dioxide upon conversion thereto. More preferably, 0.1 to 2% chlorine dioxide.

The olfactory stimulant ingredient can be a cycloaliphatic alcohol, a cycloaliphatic ketone, an aromaticnon-phenolic hydroxyl compound, an aromatic ether, a phenol having nine or more carbon atoms, or a mixture of such compounds. The olfactory stimulant ingredient can also be a mixture of volatile oils or ethereal oils derived from plant materials.

Illustrative cycloaliphatic alcohols include cyclododecanol, 3,3,5-trimethylcyclohexanol, and 4-t-butylcyclohexanol. Illustrative cycloaliphatic ketones include exaltone, fenchone, isophorone, muscone, and 3,3,5-trimethylcyclohexanone. Illustrative aromatic non-phenolic hydroxyl compounds include 1-phenylethanol, 2-phenylethanol, and 1-phenoxy-2-propanol. Illustrative aromatic ethers include diphenyl ether and 2-methoxynaphthalene. Illustrative phenols include p-t-octylphenol and 2,6-di-t-butyl-4-methylphenol.

Particularly preferred olfactory stimulant ingredients include thymol, eucalyptol, borneol, menthol, camphor, oil of *eucalyptus*, pine oil, and gum benzoin. Fixative compound when present is less volatile than the olfactory stimulant ingredient and can be, for example, an essential oil. Particularly preferred fixative compounds include oil of sweet birch, oil of spearmint, oil of pine, and cinnamon.

Certain oils extracted from plant materials include olfactory stimulants compounds as well as less volatile fixative type compounds and can serve as sources of both. Particularly preferred dual function oils of this type include basil, bergamot, lemon, citrus, jasmine, lemongrass, rosemary, sage, thyme, and vanilla.

The quantity of olfactory stimulant material in the composition of the invention is in the range from 0.01% to 3% by weight, preferably in the range from 0.05% to 1% by weight. The preferred embodiment includes at least three olfactory stimulants. The quantity of fixative material when present is in the range from 0.01% to 5% by weight, preferably in the range from 0.05% to 1% by weight.

The unsaturated fatty acid ingredient can be a monounsaturated fatty acid, such as omega-7 fatty acids and omega-9 fatty acids, or a polyunsaturated fatty acid, such as omega-3 fatty acids. The unsaturated fatty acid ingredient can also be a mixture of monounsaturated and polyunsaturated fatty acids. Preferably, the unsaturated fatty acids are derived from plant materials.

Illustrative unsaturated fatty acids include palmitoleic acid, vaccenic acid, paullinic acid, oleic acid, erucic acid, elaidic acid, gondoic acid, mead acid, nervonic acid, ximenic acid, hexadecatrienoic acid, α-linolenic acid, stearidonic acid, eicosatrienoic acid, eicosatetraenoic acid, eicosapentaenoic acid, heneicosapentaenoic acid, docosapentaenoic acid, clupanodonic acid, docosahexaenoic acid, tetracosapentaenoic acid, tetracosahexaenoic acid, linoleic acid, gamma-linolenic acid, calendic acid, eicosadienoic acid, dihomo-gamma-linolenic acid, arachidonic acid, docosadienoic acid, adrenic acid, osbond acid, tetracosatetraenoic acid, and tetracosapentaenoic acid.

Particularly preferred unsaturated fatty acid ingredients include walnut oil, clary sage seed oil, algal oil, flaxseed oil, ahiflower seed oil, borage seed oil, and sea buckthorn oil. These oils may also operate as a fixative compound.

The quantity of unsaturated fatty acid in the composition of the invention is in the range from 0.01% to 1% by weight, preferably in the range from 0.05% to 1% by weight.

The inorganic salt ingredients of the composition, i.e. alkali metal chloride, alkali metal bicarbonate, and alkali metal chlorate, can be lithium salts, potassium salts, sodium salts, and mixtures thereof. When salts of different metals are used together, for example a sodium salt and a potassium salt, ionization in the solution can associate a metal ion with the anion of a different salt from that supplied with the metal. Thus, a solution in which potassium bicarbonate and sodium chloride are dissolved contains potassium chloride as well as potassium bicarbonate, and sodium bicarbonate as well as sodium chloride.

Without intending to be bound by any theory, it is believed that the inorganic salt ingredient of the composition provides a multiplicity of functions, including adjusting the osmotic strength and the pH of the composition, and limiting the amount of water passing into the mucous membrane while enhancing the cleansing effect. It is therefore preferred to use a combination of two or more inorganic salts according to the invention.

The quantity of each inorganic salt in the composition of the invention is in the range from 0.1% to 2.5% by weight, preferably from 0.3% to 2% by weight, provided that the combined quantity of inorganic salts in the composition of the invention is in the range from 0.6% to 2.5% by weight.

Optional adjuvants that can be included in low concentrations, typically less than 0.5%, in the composition of the invention to impart desired characteristics include colorants illustrated by sodium copper chlorophyllin, surface active materials illustrated by Polysorbate 80 (an ethoxylated sorbitan ester), and chelating agents illustrated by sodium citrate.

It is a feature of the invention that the practice of nasal hygiene according to the invention requires only moderate and convenient quantities of the composition. It is sufficient for the user to place a convenient quantity of the composition, which can range from about 0.3 to 3 milliliters, into each nostril and retain it for a holding period which can range from a fraction of a minute to about ten minutes or as long as comfortable, and then remove it as by blowing the nose. Any suitable applicator can be used to place the composition inside the user's nose.

The invention claimed is:

1. A system for rinsing a human nasal passage, the system comprising:
   a mixture comprised of water, chlorine dioxide, unsaturated fatty acid, olfactory stimulant, fixative compound, and inorganic salt; and
   an apparatus for dispensing 0.3 to 3 milliliters of the mixture into a nasal passage as a mist.

2. A method of practicing nasal hygiene comprising the steps of applying to a person's nostril a mist of liquid nasal wash composition consisting essentially of the product of compounding under homogenizing conditions water, an amount of a source of chlorine dioxide sufficient to generate or provide 0.01% to 5% by weight of chlorine dioxide, 0.1 to 1% unsaturated fatty acid, 0.1 to 3% by weight of at least three olfactory stimulants; 0 to 5% by weight of at least one fixative compound; and 0.1 to 2.5% by weight of at least one inorganic salt, massaging the outside of the nostril, and blowing air out of the nostril.

* * * * *